US012728486B2

(12) United States Patent
Giachi et al.

(10) Patent No.: US 12,728,486 B2
(45) Date of Patent: Sep. 8, 2026

(54) METHOD FOR QUALITY CONTROL OF A WELDING JOINT BETWEEN A PAIR OF ENDS OF CONDUCTING ELEMENTS OF AN INDUCTIVE WINDING OF A STATOR

(71) Applicant: ATOP S.P.A., Barberino Tavarnelle (IT)

(72) Inventors: Massimiliano Giachi, San Gimignano (IT); Emanuele Angelini, Buonconvento (IT)

(73) Assignee: ATOP S.P.A., Barberino Tavarnelle (IT)

(*) Notice: Subject to any disclaimer, the term of this patent is extended or adjusted under 35 U.S.C. 154(b) by 208 days.

(21) Appl. No.: 18/835,488

(22) PCT Filed: Feb. 7, 2023

(86) PCT No.: PCT/IB2023/051078
§ 371 (c)(1),
(2) Date: Aug. 2, 2024

(87) PCT Pub. No.: WO2023/148703
PCT Pub. Date: Aug. 10, 2023

(65) Prior Publication Data

US 2025/0144749 A1 May 8, 2025

(30) Foreign Application Priority Data

Feb. 7, 2022 (IT) ........................ 102022000002090

(51) Int. Cl.
*B23K 31/12* (2006.01)
*B23K 101/38* (2006.01)
(Continued)

(52) U.S. Cl.
CPC ........... *B23K 31/125* (2013.01); *G01N 21/95* (2013.01); *G01N 21/9515* (2013.01);
(Continued)

(58) Field of Classification Search
CPC . G06T 7/0004; G06T 7/11; G06T 7/60; G06T 7/66; G06T 7/70; G06T 7/73;
(Continued)

(56) References Cited

U.S. PATENT DOCUMENTS 10,556,297 B2 * 2/2020 Kamiyama .......... B23K 31/125
12,373,940 B2 * 7/2025 Schmid ..................... G06T 7/11
(Continued)

FOREIGN PATENT DOCUMENTS

WO WO-2024241240 A1 * 11/2024 ........... B23K 31/125

OTHER PUBLICATIONS

Italian Search Report for Italian Application No. IT102022000002090 completed on Oct. 17, 2022.
(Continued)

*Primary Examiner* — Scott A Rogers
(74) *Attorney, Agent, or Firm* — Carlson, Gaskey & Olds, P.C.

(57) ABSTRACT

A method for quality control of a welding joint between a pair of ends of conducting elements of an inductive winding of a stator, the method being performed by a computer and comprising the steps that consist in:
acquiring a 3D reconstruction of the welding joint;
extracting a white 2D grayscale blob area from the 3D reconstruction of the welding join;
calculating a center of mass of the 2D grayscale blob area;
extracting a plurality of profiles from the 3D reconstruction of the welding joint);
searching for and identifying bare zones of the welding joint by analyzing one by one the profiles of the 3D reconstruction; and
calculating a bare area of the welding joint by summing the bare zones identified by the analysis of the profiles of the 3D reconstruction.

16 Claims, 12 Drawing Sheets

(51) Int. Cl.

| | |
|---|---|
| ***G01N 21/88*** | (2006.01) |
| ***G01N 21/95*** | (2006.01) |
| ***G01N 21/956*** | (2006.01) |
| ***G01N 33/207*** | (2019.01) |
| ***G06T 7/00*** | (2017.01) |
| ***G06T 7/11*** | (2017.01) |
| ***G06T 7/50*** | (2017.01) |
| ***G06T 7/60*** | (2017.01) |
| ***G06T 7/66*** | (2017.01) |
| ***G06T 7/70*** | (2017.01) |
| ***G06T 7/73*** | (2017.01) |
| ***G06T 19/00*** | (2011.01) |

(52) U.S. Cl.

CPC ..... *G01N 21/956* (2013.01); *G01N 21/95684* (2013.01); *G01N 33/207* (2019.01); *G06T 7/0004* (2013.01); *G06T 7/11* (2017.01); *G06T 7/50* (2017.01); *G06T 7/60* (2013.01); *G06T 7/66* (2017.01); *G06T 7/70* (2017.01); *G06T 7/73* (2017.01); *G06T 19/00* (2013.01); *B23K 2101/38* (2018.08); *G01N 2021/8887* (2013.01); *G01N 2203/0296* (2013.01); *G06T 2207/10028* (2013.01); *G06T 2207/20068* (2013.01); *G06T 2207/20212* (2013.01); *G06T 2207/20224* (2013.01); *G06T 2207/30108* (2013.01); *G06T 2207/30136* (2013.01); *G06T 2207/30164* (2013.01); *G06T 2219/008* (2013.01)

(58) Field of Classification Search

CPC ............... G06T 19/00; G06T 2219/008; G06T 2207/10028; G06T 2207/20068; G06T 2207/20212; G06T 2207/20224; G06T 2207/30108; G06T 2207/30136; G06T 2207/30152; G06T 2207/30164; G01N 21/8851; G01N 21/95; G01N 21/9515; G01N 21/956; G01N 21/95684; G01N 2021/8887; G01N 2021/889; G01N 2021/8893; B23K 31/125; B23K 2101/32; B23K 2101/36; B23K 2101/38; B23K 2103/12

See application file for complete search history.

(56) References Cited

U.S. PATENT DOCUMENTS

| | | | | |
|---|---|---|---|---|
| 2013/0075371 | A1 | 3/2013 | De Souza et al. | |
| 2024/0337604 | A1* | 10/2024 | Sakai | G01N 21/88 |
| 2025/0162086 | A1* | 5/2025 | Giachi | B23K 31/125 |

OTHER PUBLICATIONS

International Search Report and Written Opinion for International Application No. PCT/IB2023/051078 completed on May 16, 2023.

Vater, Johannes, et al., Quality Control and Fault Classification of Laser Welded Hairpins in Electrical Motors, Dec. 18, 2020 (Dec. 18, 2020), XP055934462, Retrieved from the Internet: URL: https://ieeexplore.ieee.org/stampPDF/getPDF.jsp?tp=&arnumber=9287701&ref=aHR0cHM6Ly9pZWVleHBsb3JlLmllZWUub3JnL2RvY3VtZW50LzkyODc3MDE=, [retrieved on Jun. 22, 2022], sections III-V.

Dupriez, Nataliya, OCT produces a better weld: Laser Focus World, Sep. 2019 (Sep. 2019), XP055934498, Retrieved from the Internet: URL: https://www.laserfocusworld.com/industrial-laser-solutions/article/14221414/octproduces-a-better-weld, [retrieved on Jun. 22, 2022], the whole document.

* cited by examiner

10°

48B

40

METHOD FOR QUALITY CONTROL OF A WELDING JOINT BETWEEN A PAIR OF ENDS OF CONDUCTING ELEMENTS OF AN INDUCTIVE WINDING OF A STATOR

The present invention relates to a method for quality control of a welding joint between a pair of ends (or terminals) of conducting elements of an inductive winding of a stator.

The method according to the present invention is particularly, although not exclusively, useful and practical in the area of quality control operations following operations to weld the conducting elements that constitute the inductive windings of stators of electric machines, for example electric motors or electric generators.

It is known that electric motors, dynamos, alternators and transformers comprise a core of ferromagnetic material on which windings are arranged which are made with electrical wires arranged according to a specific geometry. The circulation of an electric current in at least one of the windings causes, by electromagnetic induction, the circulation of an induced current in at least one other winding. Furthermore, between the ferromagnetic core and the respective windings, forces act on each other and are capable, for example, of turning a rotor with respect to a stator in an electric motor.

As said, the inductive windings described above are made using wires of electrically conducting material, generally copper. For specific applications, inductive windings are made using wire-like elements of electrically conducting material, in short conducting elements, which are first inserted in specific slots which are provided in the ferromagnetic core of the electric machine under construction and then mutually stably coupled at at least one end, typically with welding operations.

A typical example of these conducting elements is the "hairpin", where each one of the conducting elements is shaped like a fork. This fork has a pair of straight shanks which are mutually connected at one end by a bridge-like cross-piece. Typically the fork is shaped approximately like an upturned U with the bridge shaped like a cusp. Each shank of the fork, and therefore of the conducting element, has a free end for insertion in a respective slot of the ferromagnetic core of the electric machine. In particular, a first end of each conducting element is inserted into a respective first slot, while a second end of the same conducting element is inserted into a respective second slot, according to the desired logic for the inductive winding of the electric machine.

The insertion into the slots of the ferromagnetic core of the electric machine occurs by inserting the free ends of the conducting elements through longitudinal openings of the slots and making said free ends slide until they come out at the other end of the ferromagnetic core, in particular until a predefined external protrusion of the shanks is reached. So at one end of the ferromagnetic core, the bridges of the forks remain outside, while at the other end of the ferromagnetic core, the free ends of the shanks of the forks remain outside.

After insertion, the free ends of the conducting elements are bent in order to be arranged in predetermined positions, at which they are connected with other free ends of other conducting elements through welding operations. The free ends of separate conducting elements must be adjacent and arranged according to criteria for mutual alignment that make the welding operations simple and which ensure a high stability of the connection. For example, in a pair of adjacent free ends that are to be mutually connected, the first end can have a height (i.e. external protrusion) that is slightly higher than the height (i.e. external protrusion) of the second end, so that the welding operation can make a drop of molten material of the first end fall onto the second end.

The operation to weld the free ends of the conducting elements can occur by way of various welding techniques, for example with a laser beam that strikes one or both of the free ends of the conducting elements which are arranged adjacent in order to be mutually connected. Independently of the welding technique used, the melting of the material of one or both of the ends generates a welding joint that complies with the required mechanical and electrical characteristics, and therefore closes the circuit of the inductive winding according to a predefined electrical scheme.

FIG. 3 is a schematic plan view of a welding joint 16 between a pair of ends of conducting elements or hairpins of an inductive winding of a stator, where a welded area 17 and a bare area 18 can be distinguished. At the welded area 17, the welding operations have been successful and therefore in this area the two ends of the conducting elements are stably and mutually connected. By contrast, at the bare area 18, the welding operations have not been successful and therefore in this area one of the two ends of the conducting elements is uncovered, with the result that the electrical characteristics of the welding joint 16 are deteriorated.

FIG. 4 shows an example of coupled ends of a group of conducting elements or hairpins of an inductive winding of a stator, after the welding operations, where the bare areas 18 of the respective welding joints 16 between the pairs of ends of the conducting elements are highlighted by circles.

The quality of the welding operations, and consequently the quality of the welding joints 16 between the ends of the conducting elements or hairpins of an inductive winding of a stator, can be judged on the basis of various elements, including: the extent, the shape and the position of the welded area 17, with respect to the surface and to the shape of the ends of the conducting elements; the extent, the shape and the position of the bare area 18, in this case too with respect to the surface and to the shape of the ends of the conducting elements; the ratio between the extent of the welded area 17 and the extent of the bare area 18. To simplify, a welding joint 16 can be considered good quality if the welded area 17 is maximized and as a consequence the bare area 18 is minimized.

Currently, human operators, typically laboratory technicians, judge the quality (including from the aesthetic point of view) of the welding joints between the ends of the conducting elements or hairpins of an inductive winding of a stator. In particular, these operators examine these welding joints visually, basing their judgment mainly on their own professional experience and using suitable magnifying devices (for example a digital microscope) and/or measurement devices. The objective of these quality controls performed by human operators is to verify that the welding joints between the ends of the conducting elements ensure a stable and strong coupling of said ends and that they have no aesthetic defects. The operators will discard stators with defective inductive windings, or rather inductive windings that comprise conducting elements at the end of which there are defective welding joints.

However, this conventional method is not without drawbacks, among which is the fact that these quality controls performed by human operators require long times, generate high costs and imply a high risk of inaccuracies and human errors in the examination and evaluation of the welding joints.

The aim of the present invention is to overcome the limitations of the prior art described above, by devising a method for quality control of a welding joint between a pair of ends of conducting elements of an inductive winding of a stator that makes it possible to obtain better effects than those that can be obtained with conventional solutions and/or similar effects at lower cost and with higher performance levels.

Within this aim, an object of the present invention is to conceive a method for quality control of a welding joint between a pair of ends of conducting elements of an inductive winding of a stator that makes it possible to examine and evaluate welding joints objectively and rapidly.

Another object of the present invention is to devise a method for quality control of a welding joint between a pair of ends of conducting elements of an inductive winding of a stator that makes it possible to identify and calculate the bare area of the welding joints with high precision.

Another object of the present invention is to conceive a method for quality control of a welding joint between a pair of ends of conducting elements of an inductive winding of a stator that makes it possible to calculate the welded area of the welding joints with high precision.

Another object of the present invention is to devise a method for quality control of a welding joint between a pair of ends of conducting elements of an inductive winding of a stator that makes it possible to classify each welding joint according to the respective welding quality level.

Another object of the present invention is to provide a method for quality control of a welding joint between a pair of ends of conducting elements of an inductive winding of a stator that is highly reliable, easily and practically implemented, and economically competitive when compared to the prior art.

This aim and these and other objects which will become better apparent hereinafter are achieved by a method for quality control of a welding joint between a pair of ends of conducting elements of an inductive winding of a stator, said method being performed by a computer, characterized in that it comprises the steps that consist in:

- acquiring a 3D reconstruction of said welding joint;
- extracting a white 2D grayscale blob area from said 3D reconstruction of said welding joint, by transversely sectioning said 3D reconstruction with a cutting plane that is arranged at a cutting distance from a peak of said 3D reconstruction, said cutting distance being chosen so that said cutting plane is further downward than a base of said welding joint, and assigning the color white to the area of said 3D reconstruction above said cutting plane in order to determine said 2D grayscale blob area;
- calculating a center of mass of said 2D grayscale blob area in order to determine a rotation axis orthogonal to said cutting plane and passing through said center of mass;
- extracting a plurality of profiles from said 3D reconstruction of said welding joint, by longitudinally sectioning said 3D reconstruction with a plurality of planes that are orthogonal to said cutting plane, proceeding in rotation about said rotation axis, each orthogonal plane comprising a respective profile of said 3D reconstruction;
- searching for and identifying bare zones of said welding joint by analyzing one by one the profiles of said plurality of profiles of said 3D reconstruction, calculating for each profile portion a respective straight interpolation line on the points that constitute said profile portion, said profile portion being identified as a bare zone if said respective straight interpolation line has an angular coefficient with an absolute value smaller than or equal to 10°; and
- calculating a bare area of said welding joint by summing said bare zones identified by the analysis of said plurality of profiles of said 3D reconstruction, the contribution of each bare zone to said bare area being equal to an arc of an annulus comprised between said respective profile in which said bare zone has been identified and the following profile from the analysis of said plurality of profiles.

Further characteristics and advantages of the present invention will become more apparent from the description of a preferred, but not exclusive, embodiment of the method for quality control of a welding joint between a pair of ends of conducting elements of an inductive winding of a stator according to the invention, illustrated by way of non-limiting example with the aid of the accompanying drawings wherein.

Figure 7:
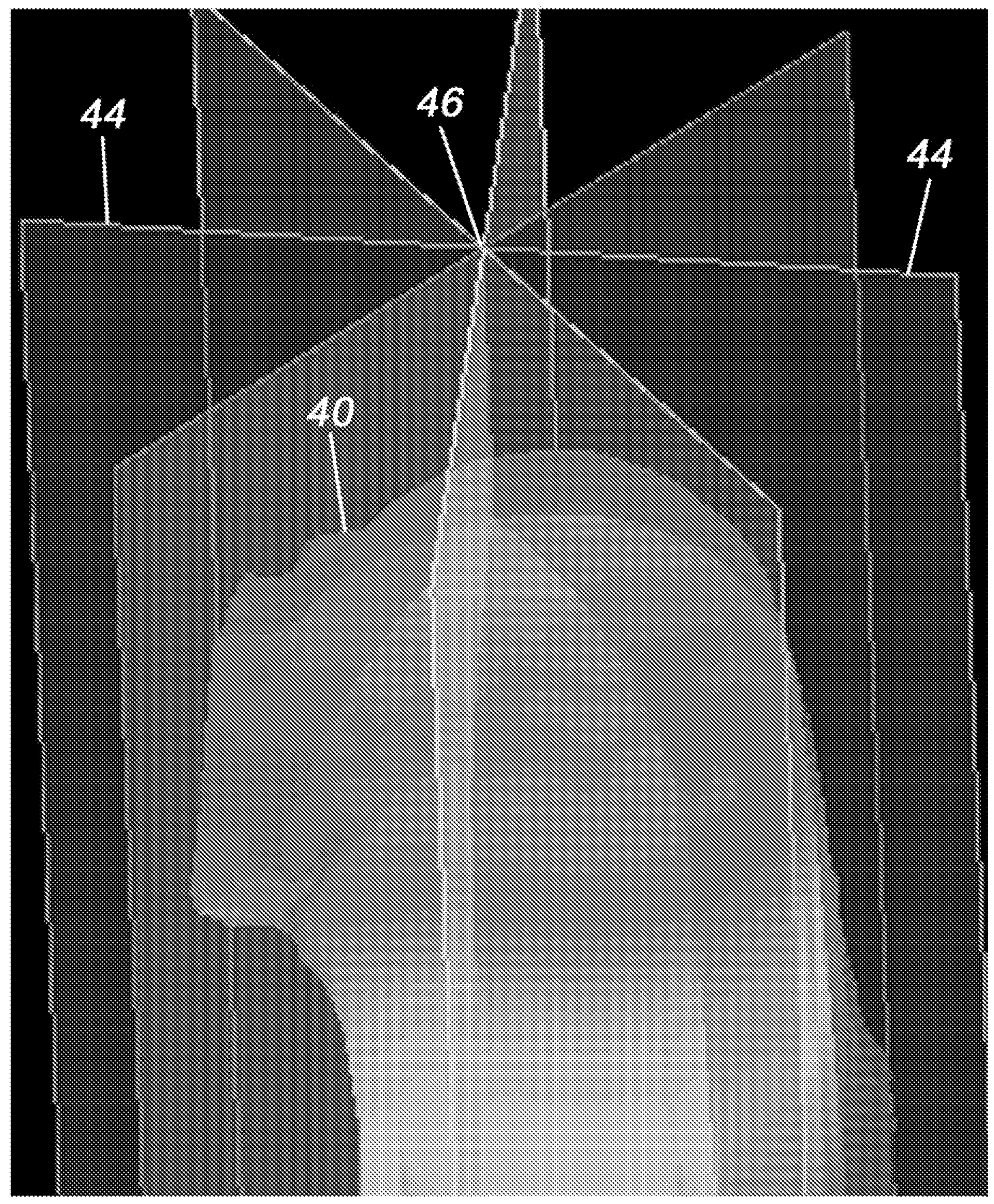
FIG. 7 is a perspective view of an example of 3D reconstruction of a welding joint between a pair of ends of conducting elements, sectioned longitudinally by four orthogonal planes.
Figures 11, 12:
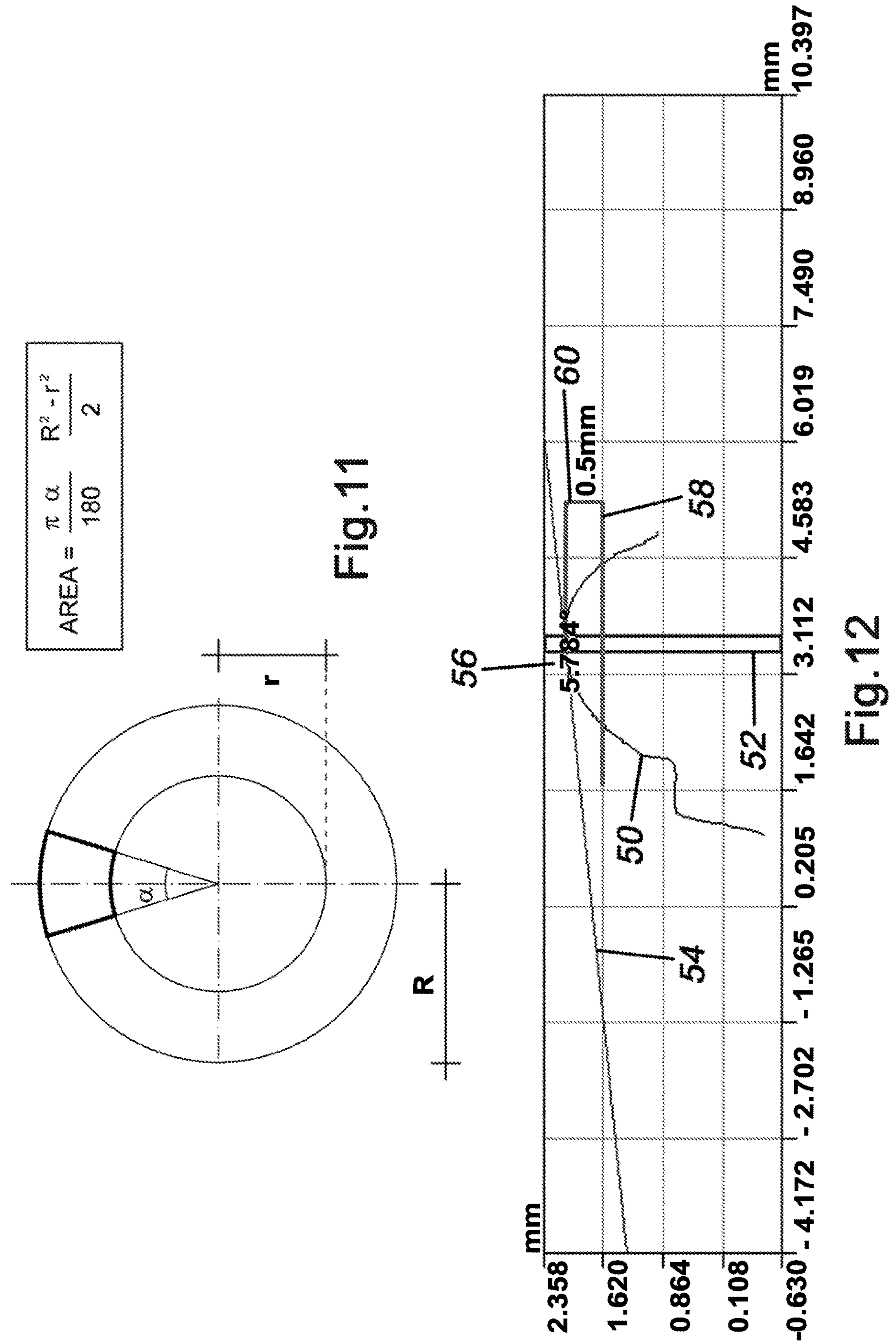
Figure 13:
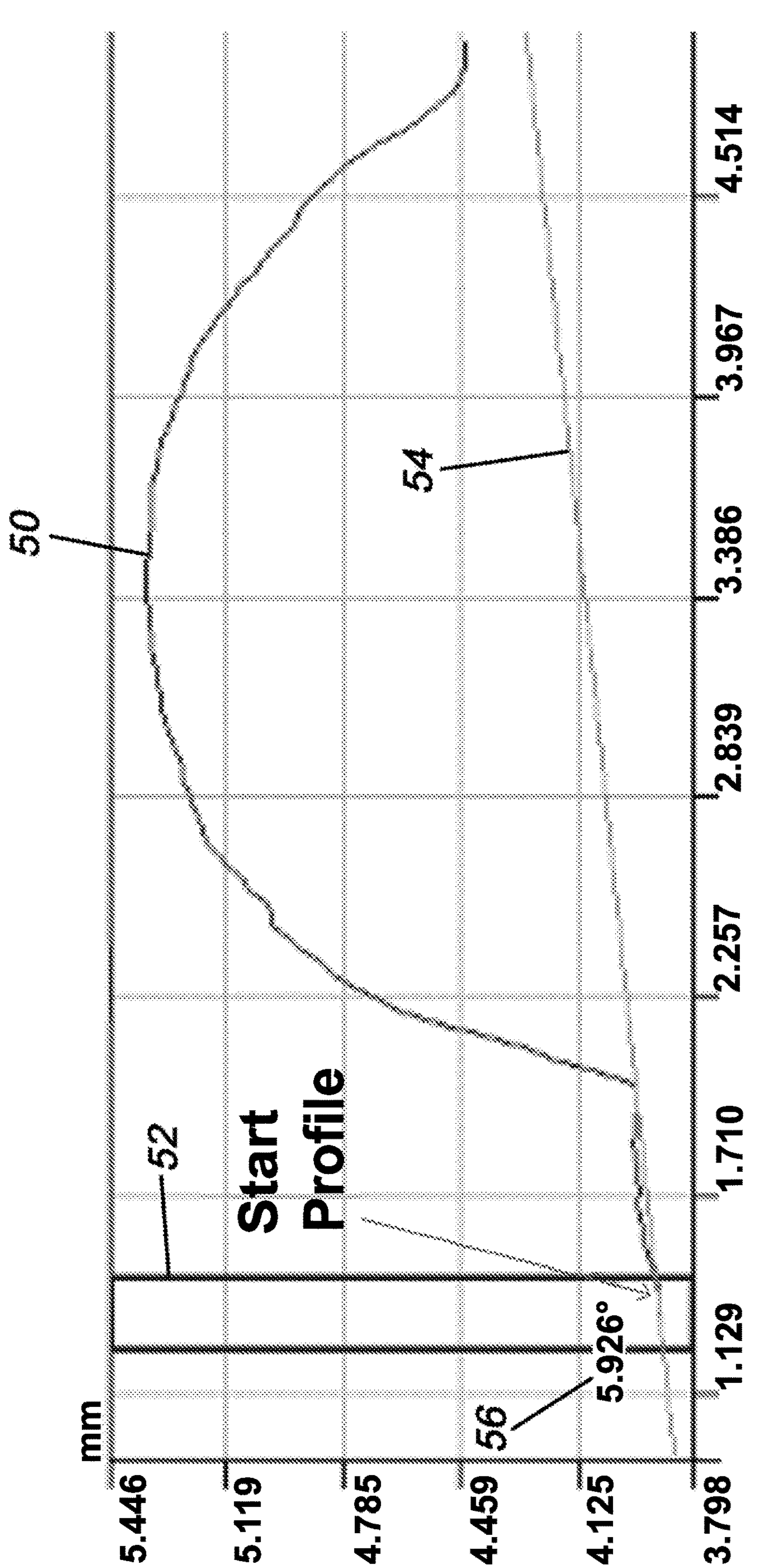

FIG. 11 graphically shows the definition of the area of an arc of an annulus and the formula for calculating that area;

FIG. 12 shows an example of an inspection window proximate to the peak of a profile of the 3D reconstruction of a welding joint shown in FIG. 7, comprising the exclusion line and the exclusion distance from the peak of the welding joint;

FIG. 13 shows an example of inspection window at the beginning of a profile of a 3D reconstruction of a welding joint.

Preliminarily, it should be noted that the method according to the present invention is executed by a data processing device or system 10, in short a computer 10, provided with suitable calculation capacity and memory.

Figure 1:
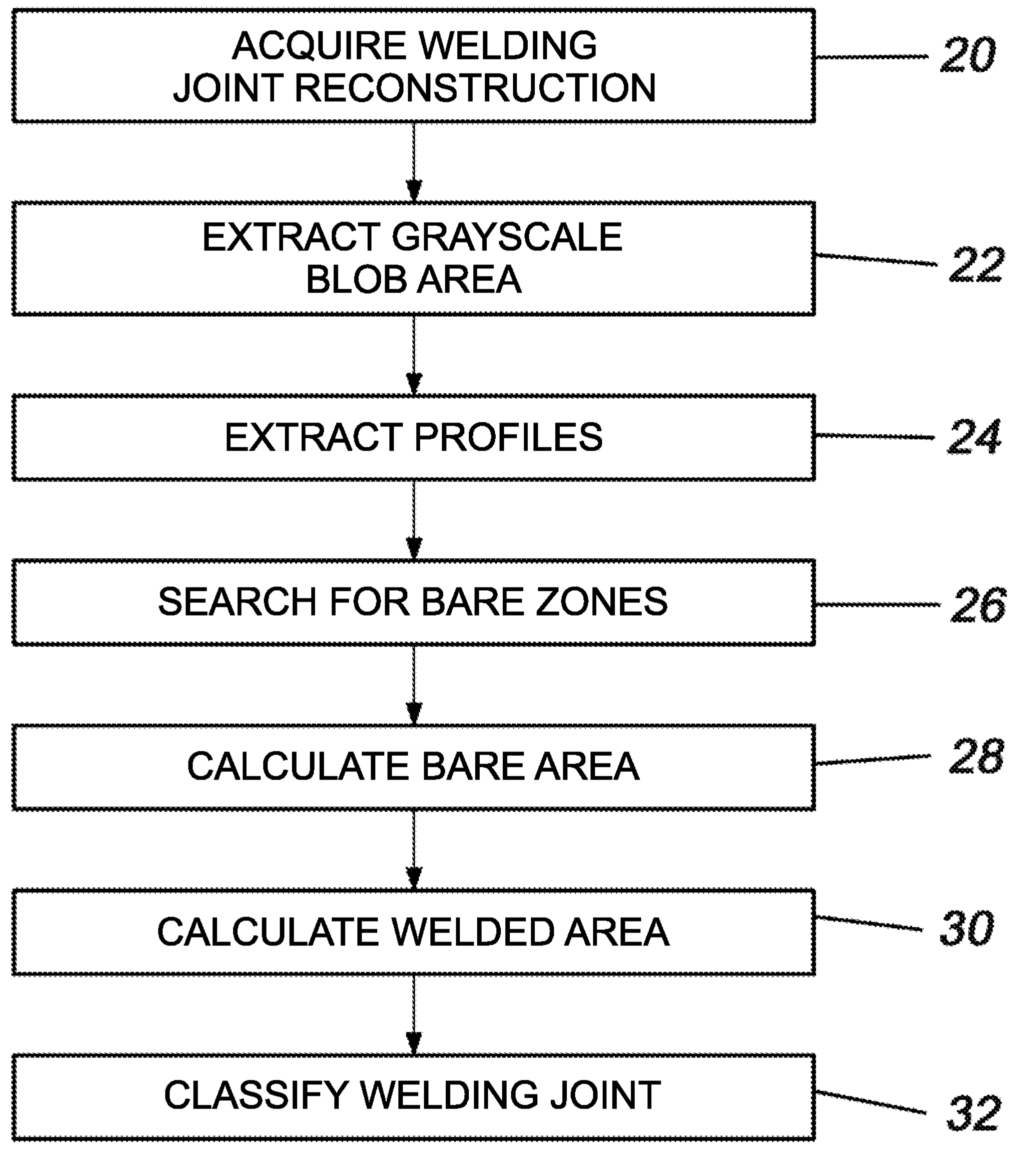
FIG. 1 is a schematic flowchart of an embodiment of the method for quality control of a welding joint between a pair of ends of conducting elements of an inductive winding of a stator according to the present invention.
Figures 2, 3:
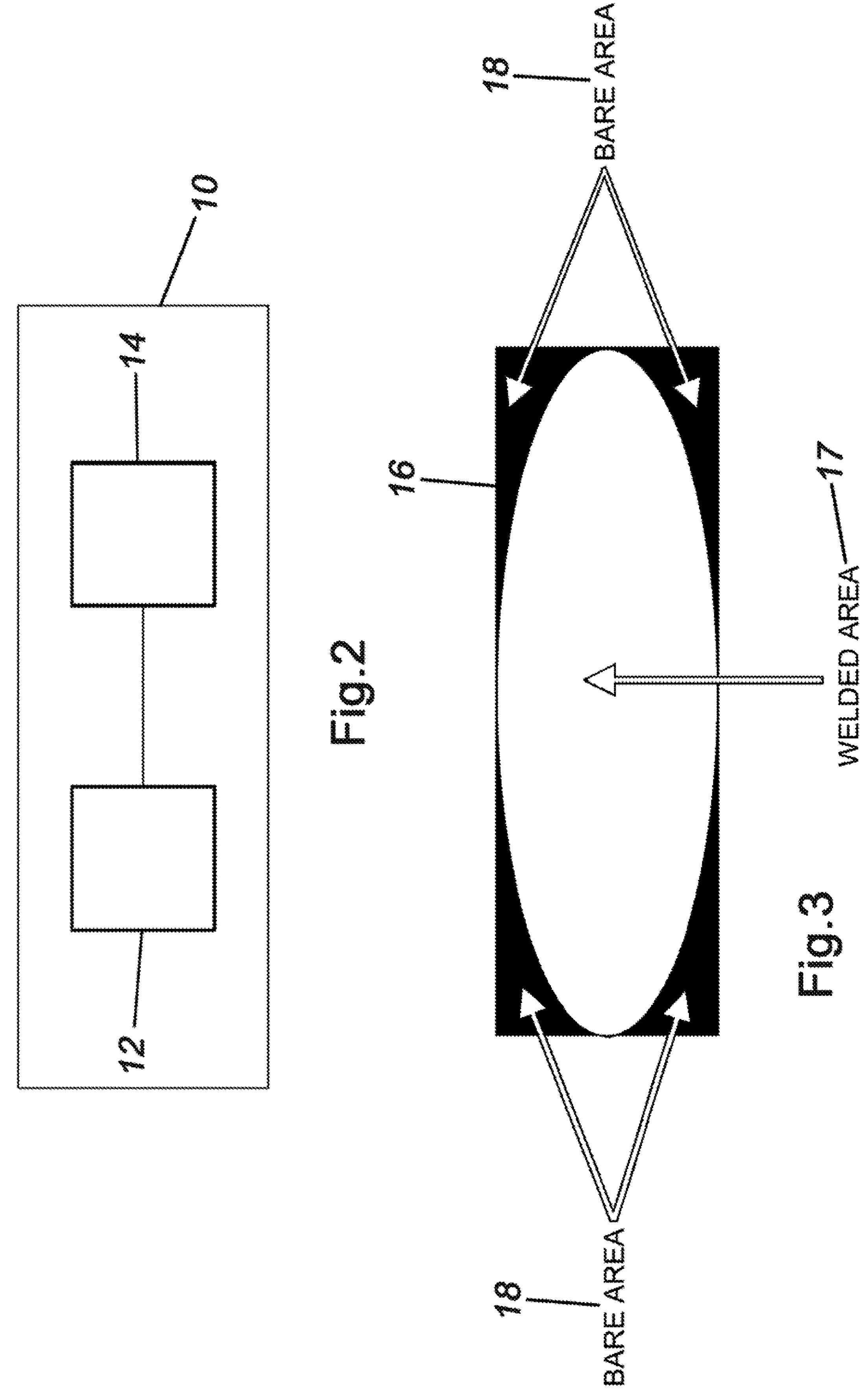
FIG. 2 is a schematic block diagram of an embodiment of the computer for executing the method for quality control of a welding joint between a pair of ends of conducting elements of an inductive winding of a stator according to the present invention.
FIG. 3 is a schematic plan view of a welding joint between a pair of ends of conducting elements of an inductive winding of a stator.
Figure 4:
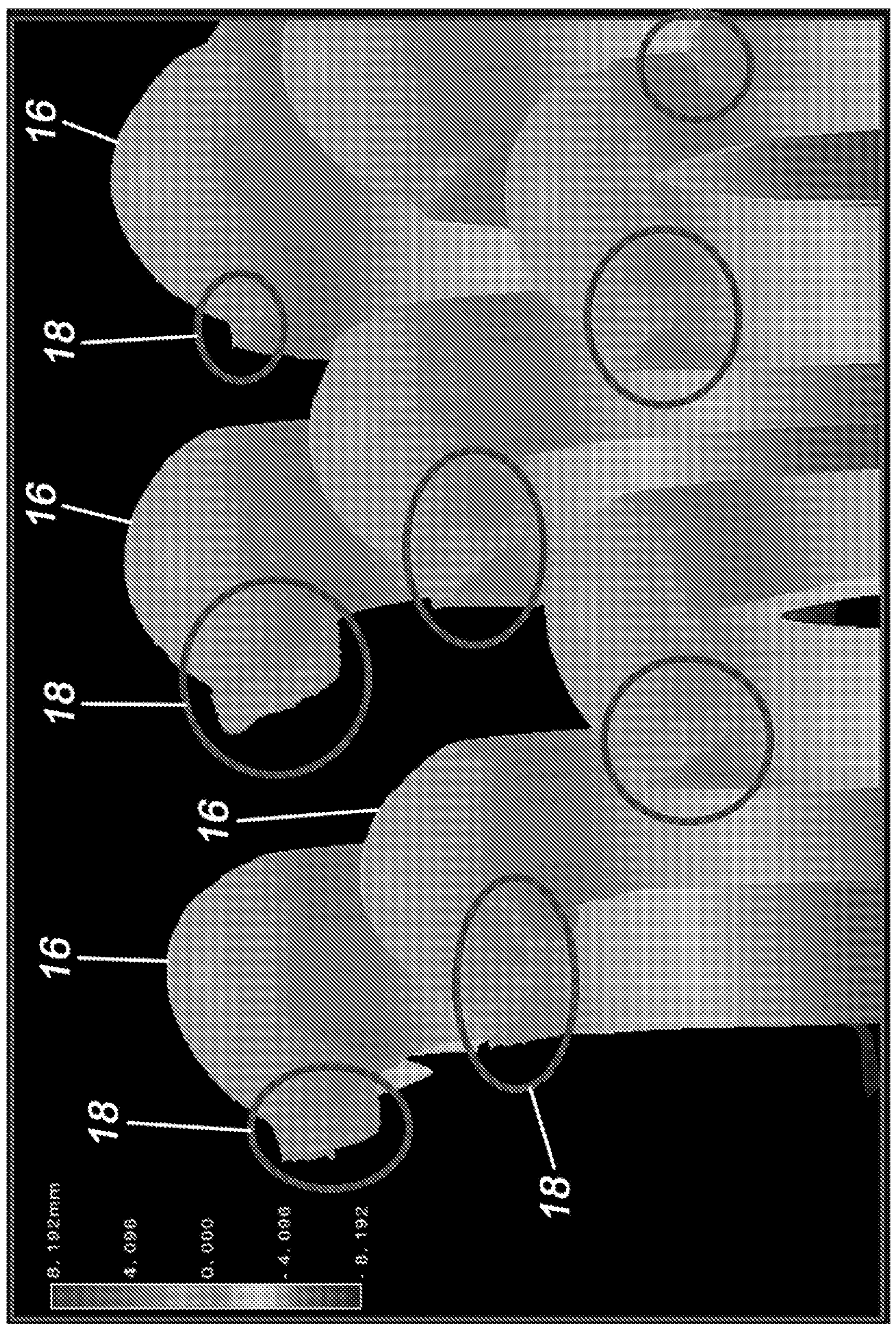
FIG. 4 is a perspective view of an example of welded ends of a group of conducting elements of an inductive winding of a stator.

With particular reference to FIG. 1, the method for quality control of a welding joint 16 between a pair of ends (or terminals) of conducting elements of an inductive winding of a stator according to the present invention comprises substantially the following steps.

Initially, in step 20, a three-dimensional (3D) reconstruction 40 of the welding joint 16 to be examined and evaluated is acquired, this 3D reconstruction 40 being in the form of a depth map.

Preferably, the acquisition of the 3D reconstruction 40 of the welding joint 16 is executed with the pair of ends of conducting elements of said welding joint 16 oriented vertically and with the base of the ends pointing upward. Preferably, the welding joint 16 between the pair of ends of conducting elements and the 3D reconstruction 40 of said welding joint 16 have the same orientation with respect to a common geometric reference system.

The 3D reconstruction 40 of the welding joint 16 can be generated and originate from a 3D vision device or system, for example a 3D camera or a 3D laser scanning device. The 3D vision device or system can be operatively connected to the computer 10 that executes the method according to the invention; in this case the computer 10 is also provided with suitable capacities for interfacing with the 3D vision device or system, and vice versa.

Advantageously, the 3D reconstruction 40 of the welding joint 16 can be made using the Fringe Pattern Projection technique. Therefore, the 3D vision device or system can use the Fringe Pattern Projection technique. This technique is briefly described as follows: a set of light patterns is projected onto a worktop (in this case where the stator with the inductive winding is arranged) and a 3D sensor reconstructs a 3D object (in this case the welding joints 16 of the hairpins of the inductive winding) following the analysis of the reflections of said light patterns.

In step 22, a white two-dimensional (2D) grayscale blob area 42 is extracted or obtained from the 3D reconstruction 40 of the welding joint 16 of the preceding step 20. In general, in artificial vision, also known as computer vision, a blob is a group of pixels of an image that relate to each other in that they share one or more common properties.

To extract or obtain this 2D grayscale blob area 42, the 3D reconstruction 40 of the welding joint 16 is sectioned transversely by a cutting plane 41 arranged at a chosen cutting distance 39 from the peak (highest point) of said 3D reconstruction 40 of the welding joint 16. In particular, this cutting distance 39 is comprised between 1 mm and 6 mm, and preferably comprised between 2 mm and 3 mm. This cutting distance 39 is chosen so that the transverse cross-section 41, i.e. the cutting plane 41, mentioned above is always further downward, along the Z axis, with respect to the base of the welding joint 16. The cutting distance 39 can be chosen by a human operator, therefore it can be parametrized.

Figure 5:
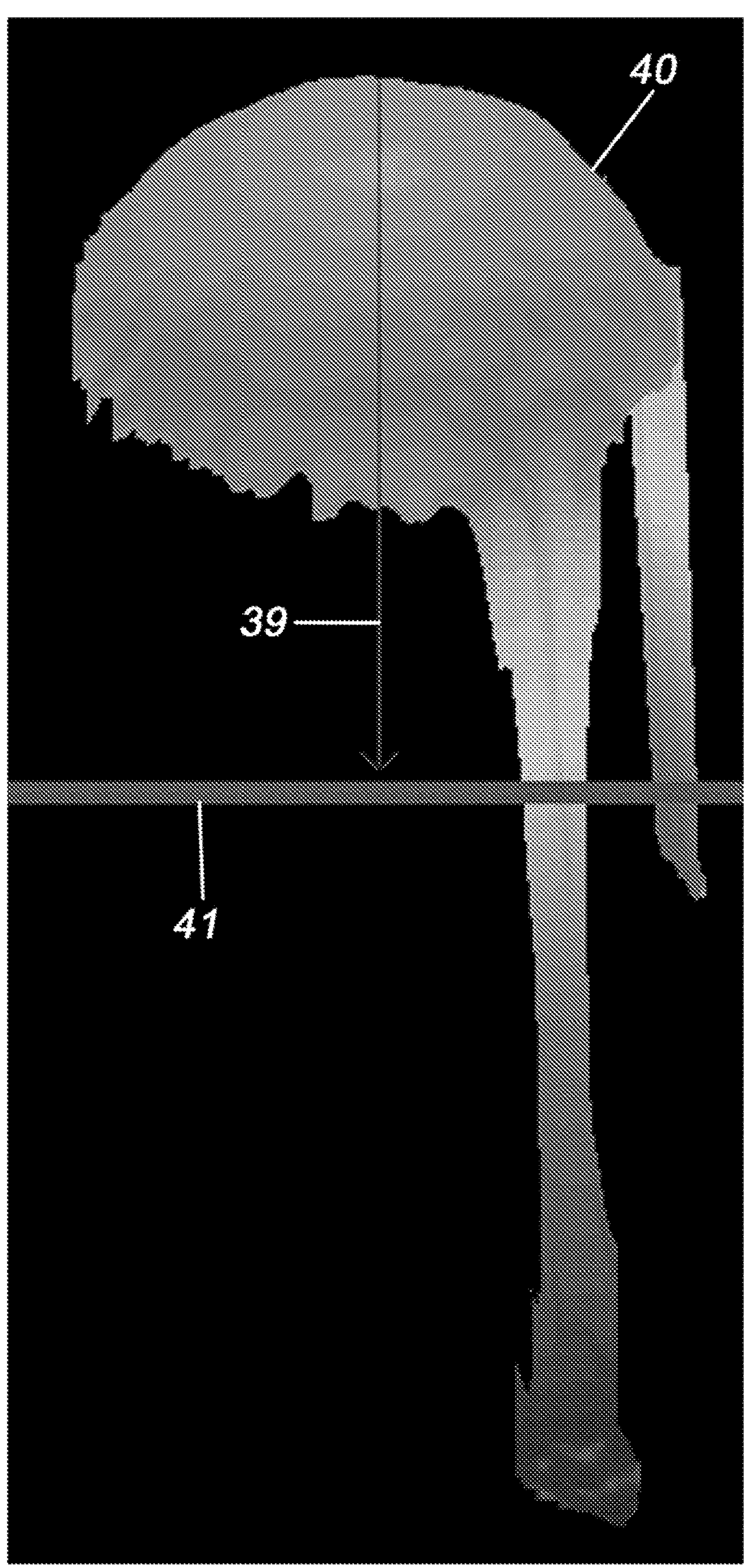
FIG. 5 is a front elevation view of an example of 3D reconstruction of a welding joint between a pair of ends of conducting elements, sectioned transversely by a cutting plane.

FIG. 5 shows an example of 3D reconstruction 40 of a welding joint 16 between a pair of ends of conducting elements, where the transverse cross-section 41 is illustrated by a horizontal segment, and where the cutting distance 39 between the peak and the transverse cross-section is illustrated by a vertical arrow.

The plane resulting from the transverse sectioning operation of the 3D reconstruction 40 of the welding joint 16 is called a cutting plane 41 because it "cuts" said 3D reconstruction 40 of the welding joint 16 into two portions, one upper portion (above the cutting plane 41) and one other lower portion (below the cutting plane 41).

Furthermore, to extract or obtain this 2D grayscale blob area 42, following the transverse sectioning of the 3D reconstruction 40 of the welding joint 16, the color white is assigned to the area of said 3D reconstruction 40 above the cutting plane 41 in order to determine the 2D grayscale blob area 42.

The grayscale image of the cutting plane 41 comprises a two-dimensional representation of everything that is above the cutting plane 41 in white, and everything that is below the cutting plane 41 in black (the background on the other hand is represented in gray). The 2D grayscale blob area 42, of interest in the scope of the invention, for example expressed in $mm^2$, is the white-colored area of the grayscale image of the cutting plane 41.

As can be observed for example in FIG. 5, it is frequently the case that the cutting plane 41 is at a portion of the 3D reconstruction 40 of the welding joint 16 where said 3D reconstruction 40 is incomplete. In this case, advantageously, the upper portion of the 3D reconstruction 40 of the welding joint 16 is projected (orthogonal projection) on the cutting plane 41.

Figure 6A:
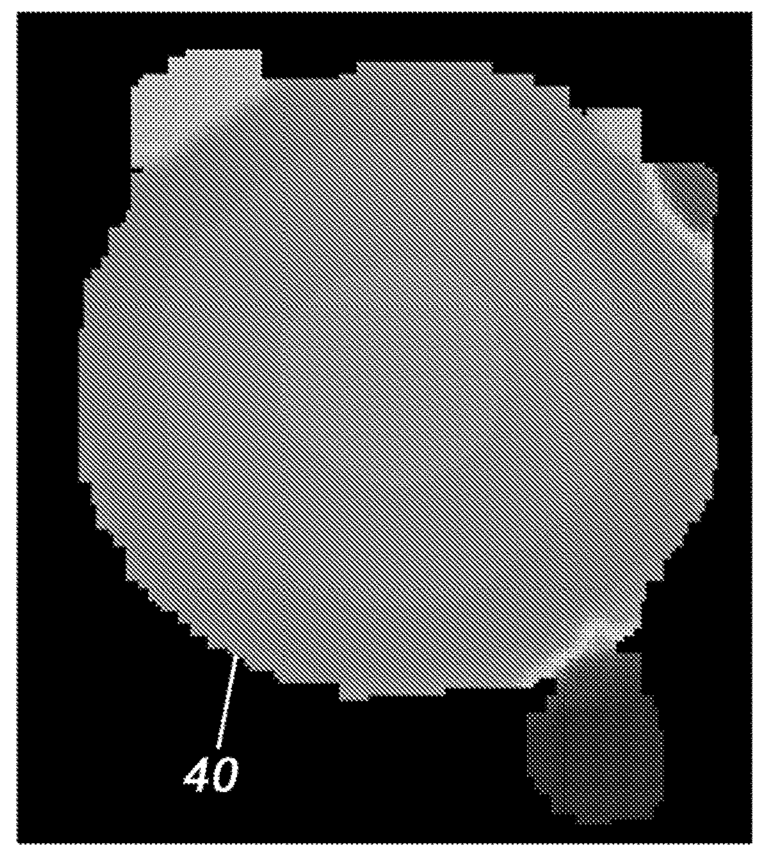
FIGS. 6A and 6B are respectively a plan view and a grayscale cutting plane of the 3D reconstruction of a welding joint shown in FIG. 5.
Figure 6B:
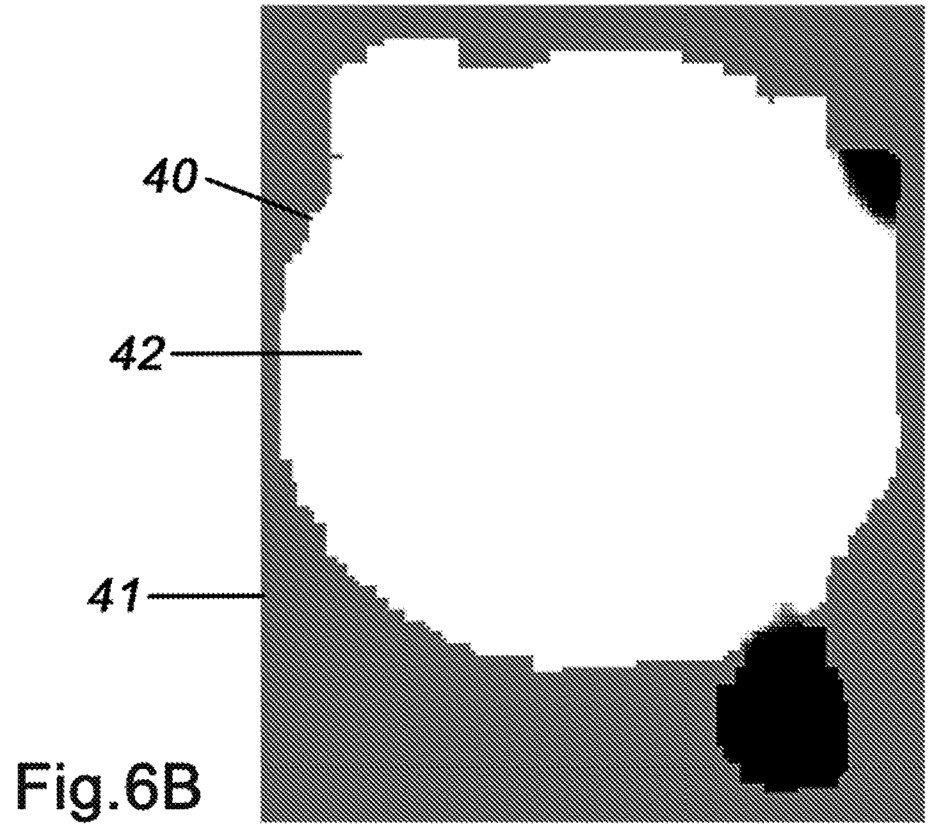

FIG. 6A is a plan view of the 3D reconstruction 40 of a welding joint 16 shown in FIG. 5. FIG. 6B shows the cutting plane 41, in grayscale, of the 3D reconstruction 40 of a welding joint 16 shown in FIG. 5, where the above mentioned orthogonal projection has been executed.

Subsequently, a center of mass or center of gravity is calculated of the 2D grayscale blob area 42 of the preceding step 22, in order to determine a rotation axis 46 orthogonal to the cutting plane 41 and passing through said center of mass.

In step 24, a plurality of profiles 50 is extracted or obtained from the 3D reconstruction 40 of the welding joint 16 of the preceding step 20. In particular, the 3D reconstruction 40 of the welding joint 16 is longitudinally sectioned by a plurality of planes 44 that are orthogonal to the cutting plane 41, as many as there are profiles 50, proceeding in rotation about the rotation axis 46. In practice, the center of mass or center of gravity of the 2D grayscale blob area 42 of the preceding step 22 is used to determine the rotation axis 46 of the various longitudinal cross-sections, i.e. of the various planes 44 that are orthogonal to the cutting plane 41. Each plane 44 of the plurality of planes that are orthogonal to the cutting plane 41 which is produced by the above longitudinal sectioning operation comprises a respective representation in two dimensions of the profile 50 of the 3D reconstruction 40 of the welding joint 16 longitudinally sectioned by said plane.

FIG. 7 shows an example of 3D reconstruction 40 of a welding joint 16 between a pair of ends of conducting elements, sectioned longitudinally by four planes 44 that are orthogonal to the cutting plane 41. FIGS. 9A to 9E show a profile 50 of the 3D reconstruction 40 of a welding joint 16 shown in FIG. 7.

Preferably, the orthogonal planes 44 longitudinally sectioning the 3D reconstruction 40 of the welding joint 16 are uniformly distributed in breadth, i.e. by rotating with respect to each other through a chosen breadth A, for example 10°, until a total breadth of no more than 179° is reached (starting from) 0°. The breadth of rotation A can be chosen by a human operator, therefore it can be parametrized. In other words, a subsequent orthogonal plane 44 is rotated through a breadth A, for example by 10°, with respect to a preceding orthogonal plane 44. Basically, assuming a breadth of rotation A of 10°, the first profile 50 of the 3D reconstruction 40 is extracted from an orthogonal plane 44 longitudinally sectioning at 0°, then the second profile 50 is extracted from an orthogonal plane 44 longitudinally sectioning at 10°, and so on until an orthogonal plane 44 longitudinally sectioning at 170°. The rotation of the longitudinally sectioning planes 44, which are orthogonal to the cutting plane 41, can be clockwise or anticlockwise.

Figures 8A, 8B:
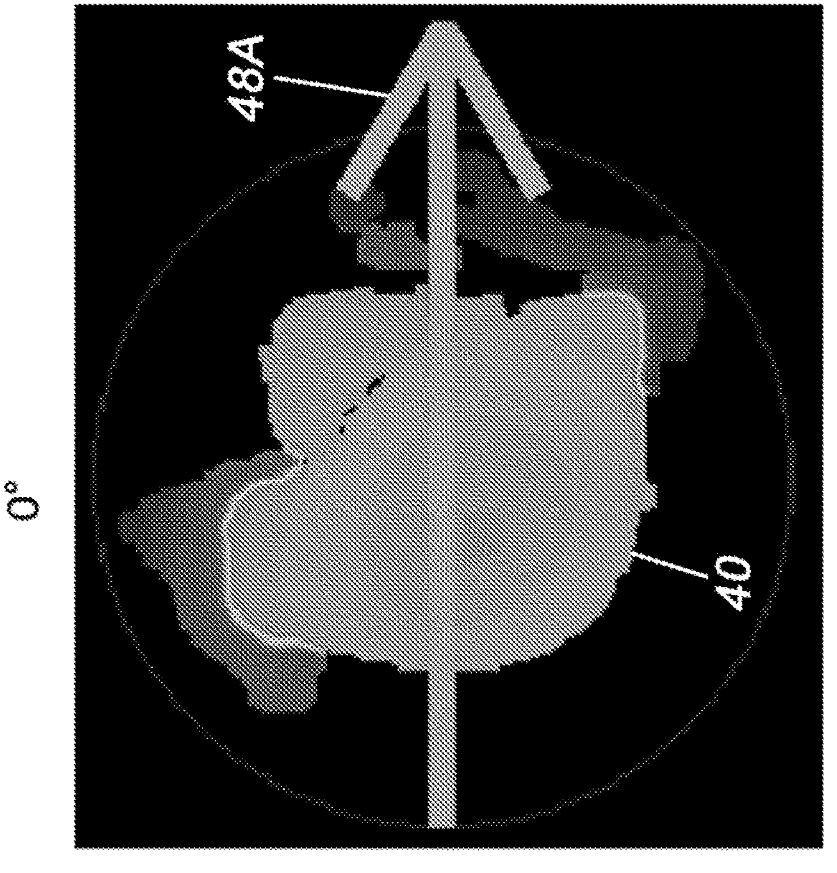
FIGS. 8A and 8B are plan views of an example of 3D reconstruction of a welding joint between a pair of ends of conducting elements, sectioned longitudinally respectively by a first and a second orthogonal plane.

FIGS. 8A and 8B show an example of 3D reconstruction 40 of a welding joint 16 between a pair of ends of conducting elements, longitudinally sectioned respectively by a first orthogonal plane 44 at 0° and a second orthogonal plane 44 at 10°, therefore with a breadth of rotation A of 10° between the first and the second.

In step 26, bare zones 62 of the welding joint 16 are searched for and identified by analyzing, one by one, the profiles 50 of the plurality of profiles of the 3D reconstruction 40 of the welding joint 16 of the preceding step 24. In particular, in each profile 50, profile portions 50 are searched for in which the straight interpolation line 54 calculated on the points that constitute the profile portion 50 has an angular coefficient 56 with an absolute value close to zero. In particular, this angular coefficient 56 is less than or equal to 10° (i.e. comprised between +10° and)−10°, preferably less than or equal to 5° (i.e. comprised between +5° and)−5°, and even more preferably less than or equal to 3° (i.e. comprised between +3° and −3°). The angular coefficient 56 can be chosen by a human operator, therefore it can be parametrized. The angular coefficient 56 of the straight interpolation line 54 indicates the slope of the analyzed profile portion 50. If the angular coefficient 56 of the straight interpolation line 54, and therefore the slope of the profile portion 50, has an absolute value close to zero, then said profile portion 50 is identified as a bare zone 62 of the welding joint 16. Note that the lower the absolute value of the limit of the angular coefficient 56, the fewer the number of bare zones 62 identified in the welding joint 16; and, vice versa, the higher the absolute value of the limit of the angular coefficient 56, the higher the number of bare zones 62 identified in the welding joint 16.

Advantageously, a sequence of inspection windows 52, arranged side by side one after the other, each one of preset width L, for example 0.234 mm, slides along each profile 50 of the 3D reconstruction 40 of the welding joint 16, in particular from the beginning to the end of the profile 50. In any case, the width L of the inspection windows 52 is less than the width of the profile 50. The width L of the inspection windows 52 can be chosen by a human operator, therefore it can be parametrized. The advancement between one inspection window 52 and a subsequent inspection window 52 is equal to the width L. Basically, assuming a sliding of the inspection windows 52 from left to right (along the direction of the arrows 48A and 48B shown in FIGS. 8A and 8B): the first inspection window 52 is arranged at the initial portion of the profile 50; the second inspection window 52 is arranged immediately to the right of the first inspection window 52, i.e. the left end of the second inspection window 52 is superimposed on the right end of the first inspection window 52; and so on until the last inspection window 52 is arranged at the end portion of the profile 50. Alternatively, the sliding of the inspection windows 52 can be from right to left.

For each inspection window 52, a straight interpolation line 54 is calculated on the points that constitute the profile portion 50 contained within said inspection window 52. The angular coefficient 56 of this straight interpolation line 54 indicates the slope of the profile portion 50 contained within the inspection window 52. If the angular coefficient 56 of the straight interpolation line 54 for the inspection window 52, and therefore the slope of the profile portion 50 contained in the inspection window 52, has a sufficiently small absolute value, then said profile portion 50 contained in said inspection window 52 is identified as a bare zone 62 of the welding joint 16.

FIGS. 9A to 9E show an example of sequence of inspection windows 52 along a profile 50 of the 3D reconstruction 40 of a welding joint 16 shown in FIG. 7, where the profile 50, the respective inspection window 52 and the respective straight interpolation line 54 are shown. As can be observed from FIGS. 9C and 9D, in this example the bare zones 62 of the welding joint 16 are identified when the straight interpolation line 54 of the profile portion 50 contained within the inspection window 52 has an angular coefficient 56 less than or equal to 3°.

However, not all the zones where the angular coefficient 56 of the straight interpolation line 54, and therefore the slope of the profile portion 50, has an absolute value close to zero should be identified as bare zones 62. In fact, if the above criteria are followed blindly, then even the zones located proximate to the peak of the welding joint 16 are identified as bare zones 62, but in fact they should be excluded even though they have a slope close to zero, because the peak of the welding joint 16 is substantially flat as such.

To resolve this drawback, advantageously, still in step 26, an exclusion plane is arranged which transversely sections the 3D reconstruction 40 of the welding joint 16, thus also positioning a corresponding exclusion line 58 in the plurality of profiles 50 of said 3D reconstruction 40. The exclusion plane and the corresponding exclusion line 58 are arranged at a chosen exclusion distance 60, for example 0.5 mm, from the peak of the welding joint 16. The exclusion distance 60 can be chosen by a human operator, therefore it can be parametrized. Furthermore, for each profile portion 50, for example contained in an inspection window 52, the average height of the points that constitute the profile portion 50 is also calculated. In this way, all the zones (bare and otherwise) that are located above the exclusion plane, i.e. at an average height higher than the height of said exclusion plane, are excluded or ignored. Similarly, all the profile portions 50 that are located above the exclusion line 58, i.e. at an average height higher than the height of the exclusion line 58, are excluded or ignored. As a consequence, zones located proximate to the peak of the welding joint 16 with a slope with an absolute value close to zero are not identified as bare zones 62.

FIG. 12 shows an example of inspection window 52 proximate to the peak of a profile 50 of the 3D reconstruction 40 of a welding joint 16 shown in FIG. 7, where the exclusion line 58 and the exclusion distance 60 from the peak of the welding joint 16 are shown.

However, this approach, which excludes the zones located proximate to the peak of the welding joint 16, without further contrivances, leads to completely incorrect results if the welding joint 16 is substantially missing (i.e. the wires are completely bare). In practice, if the difference in height between the two ends of conducting elements is less than the exclusion distance 60 chosen to ignore all the zones (bare and otherwise) proximate to the peak of the welding joint 16, then paradoxically a pair of ends of conducting elements that are not welded (i.e. wires completely bare) would be considered a good-quality welding joint 16.

To solve this drawback, advantageously, still in step 26, all the bare zones 62 identified in the welding joint 16 are counted, i.e. both the ones above and the ones below the exclusion plane, if any. If the total number of bare zones 62 is greater than a chosen percentage, for example 65%, of the number of analyzed profile portions 50, i.e. of the number of active inspection windows 52 (i.e. windows inside which there is at least one point of the profile 50), then all of the welding joint 16 is identified as a bare area 18 (welded area=0, bare area=2D grayscale blob area). The above mentioned percentage can be chosen by a human operator, therefore it can be parametrized.

In step 28, the bare area 18 of the welding joint 16 is calculated starting from the bare zones 62 identified by the analysis of the plurality of profiles 50 of the 3D reconstruction 40 of the welding joint 16 of the preceding step 26. Note that each bare zone 62 of the welding joint 16, identified in any profile 50 of the 3D reconstruction 40, contributes to the bare area 18 of said welding joint 16. In particular, the contribution of each bare zone 62 to the bare area 18 of the welding joint 16 is equal to the arc of an annulus comprised between the profile 50 of the 3D reconstruction 40 in which the bare zone 62 has been identified and the subsequent profile 50 of the 3D reconstruction 40 among those analyzed. In general, the area of an arc of an annulus is defined and calculated as shown in FIG. 11, from which the following formula is cited:

$$\text{AREA} = [(\pi \times \alpha)/180] \times \left[\left(R^2 - r^2\right)/2\right]$$

Figures 9A, 9B:
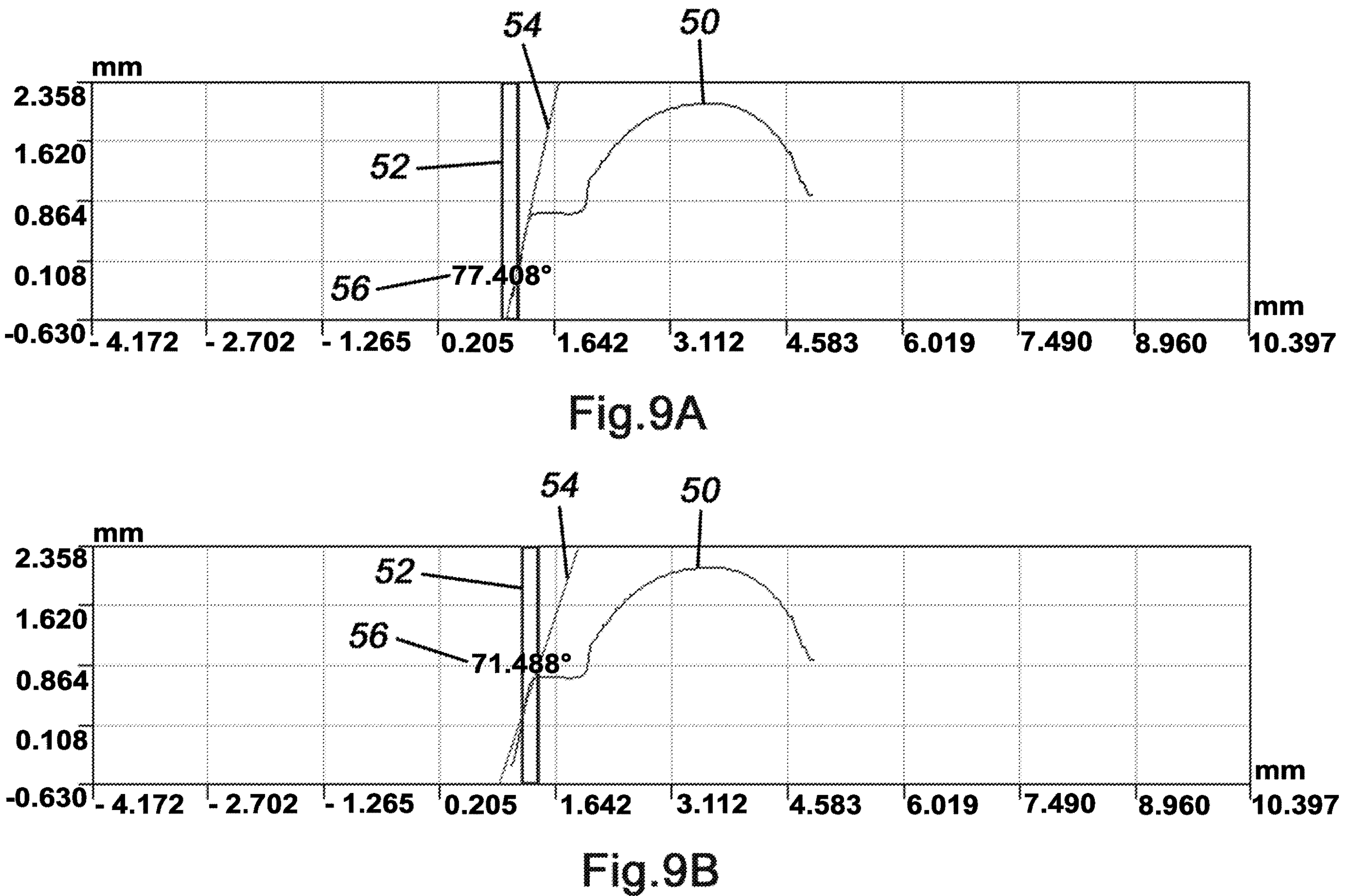
FIGS. 9A to 9E show an example of a sequence of inspection windows along a profile of the 3D reconstruction of a welding joint shown in FIG. 7, each one of these figures comprising the profile, the respective inspection window and the respective straight interpolation line.
Figures 9C, 9D:
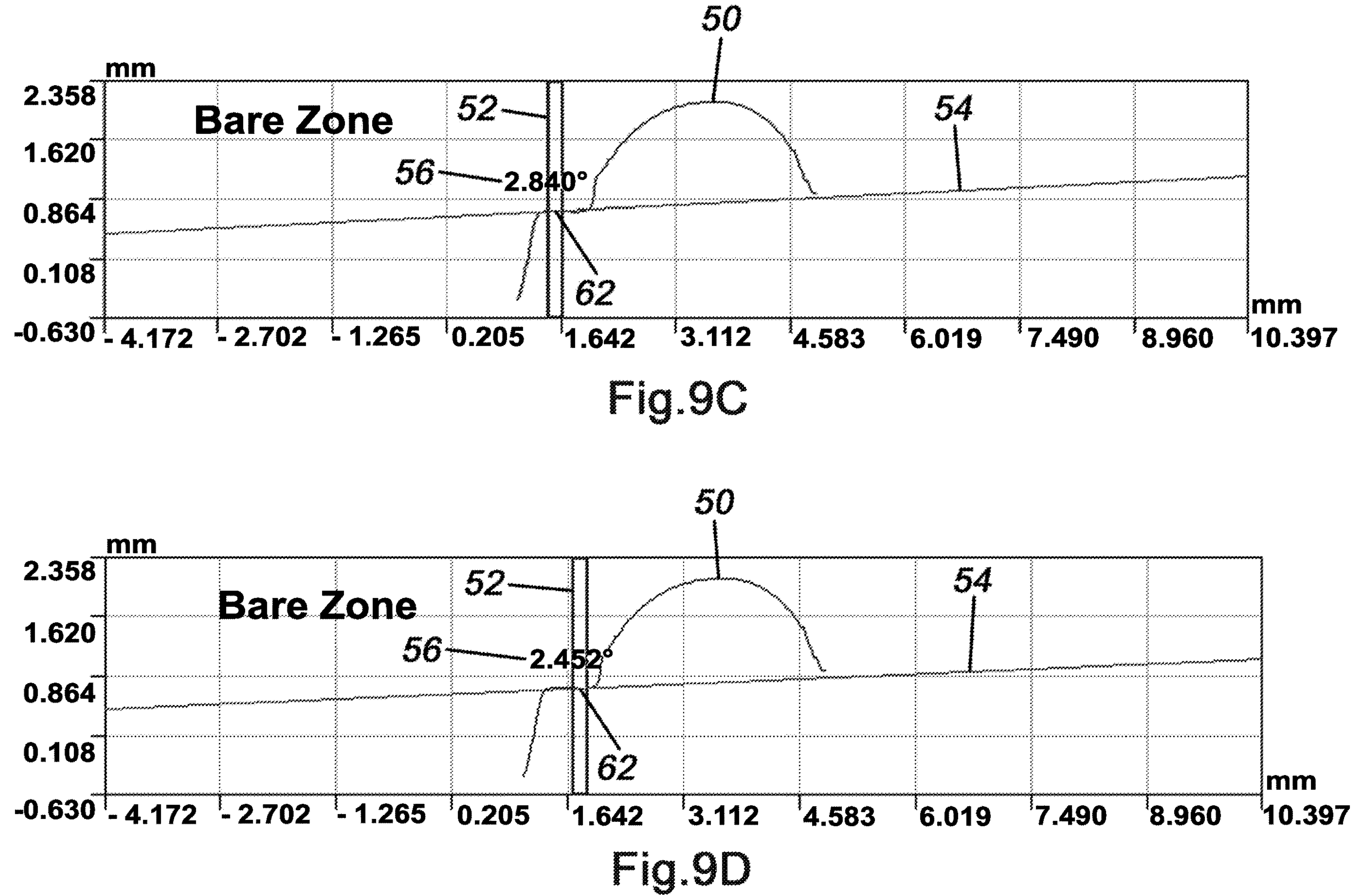
Figures 9E, 10:
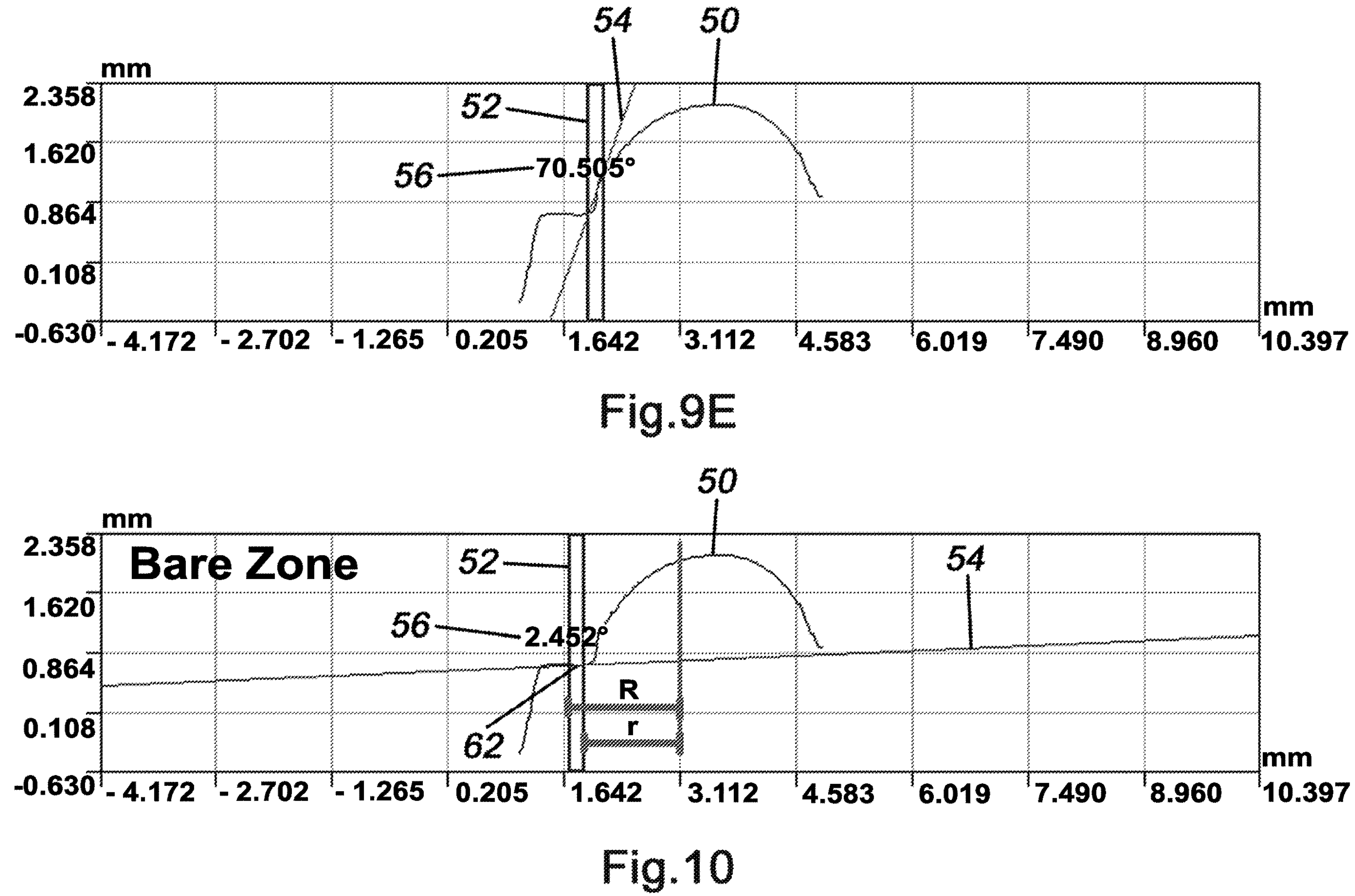
FIG. 10 is based on FIG. 9D above, graphically showing the radii R and r for calculating the area of an arc of an annulus corresponding to a bare zone of the welding joint.

FIG. 10 shows an example of inspection window 52 along a profile 50 of the 3D reconstruction 40 of a welding joint 16 shown in FIG. 7, where the profile 50, the inspection window 52 and the straight interpolation line 54 are shown, and where the radii R and r for calculating the area of an arc of an annulus corresponding to a bare zone 62 of the welding joint 16 are also shown.

With particular reference to FIGS. 10 and 11, within the scope of the invention, we have:

- the angle α between the two segments that contain the arc of an annulus corresponding to a bare zone 62 of the welding joint 16 is equal to the breadth of rotation A between two adjacent orthogonal planes 44, and therefore between two respective adjacent profiles 50, of the 3D reconstruction 40 of the welding joint 16;
- the radius R is equal to the distance between the center of mass or center of gravity of the 2D grayscale blob area 42 of step 22 and the end of the inspection window 52 furthest from it (taking the profile 50, the left end if the inspection window 52 is to the left of the center of mass, or the right end if the inspection window 52 is to the right of the center of mass); and
- the radius r is equal to the distance between the center of mass or center of gravity of the 2D grayscale blob area 42 of step 22 and the end of the inspection window 52 closest to it (taking the profile 50, the right end if the inspection window 52 is to the left of the center of mass, or the left end if the inspection window 52 is to the right of the center of mass).

Applying the above formula for each bare zone 62 identified, its corresponding contribution, for example expressed in $mm^2$, to the bare area 18 of the welding joint 16 is calculated. Therefore, the bare area 18, for example expressed in $mm^2$, of the welding joint 16 is equal to the sum of all the contributions of all the bare zones 62 identified in the various profiles 50 of the 3D reconstruction 40.

Advantageously, in step 28, if a profile portion 50 contained in an inspection window 52 which is at the beginning or at the end of the profile 50 is identified as a bare zone 62, its contribution to the bare area 18 is weighed on the filling percentage of the respective inspection window 52 by said profile portion 50. Often, in fact, the inspection windows 52 at the beginning or at the end of the profile 50 are not completely filled by the respective profile portions 50, i.e. the start or end point of the profile 50 does not correspond to the start or end of the inspection window 52.

FIG. 13 shows an example of inspection window 52 at the beginning of a profile 50 of a 3D reconstruction 40 of a welding joint 16.

Preferably, in step 30, the welded area 17 of the welding joint 16 is calculated by subtracting the bare area 18 of the welding joint 16 of the preceding step 28 from the 2D grayscale blob area 42 of step 22, in accordance with the following formula:

$$\text{welded area} = 2D \text{ grayscale blob area} - \text{bare area}$$

Advantageously, in step 32, the welding joint 16 is classified according to its welding quality level, for example in a scale of values from 1 to 10 where level 10 corresponds to a welding joint 16 that is substantially perfect and level 1 corresponds to a welding joint 16 that is substantially missing (i.e. wires completely bare). The quality level of the welding joint 16 can be evaluated on the basis of the value of the welded area 17 calculated in the preceding step 30, the value of the bare area 18 calculated in the preceding step 28, and/or the ratio between the value of the welded area 17 and the value of the bare area 18. The welding quality levels can be defined by a human operator or adapted to known quality standards.

Obviously, the method described above for quality control of a welding joint 16 between a pair of ends of conducting elements can be performed on each welding joint 16 of an inductive winding of a stator. On the basis of the tests conducted, the execution of the method described above on a welding joint 16 between a pair of ends of conducting elements takes approximately 0.6 s and has an average standard deviation of approximately 0.09 $mm^2$.

The present invention also relates to a data processing device or system, in short a computer, generally designated by the reference numeral 10, which comprises means 12, 14 which are configured to execute the steps described above of the method for quality control of a welding joint 16 between a pair of ends of conducting elements of an inductive winding of a stator according to the invention. In particular, the computer 10 comprises a processor 12 and a memory 14. The computer 10 can be operatively connected to a 3D vision device or system which is configured to generate a 3D reconstruction 40 of the welding joint 16 to be examined and evaluated; in this case the computer 10 also comprises a module for interfacing with the 3D vision device or system, and vice versa.

The present invention also relates to a computer program that comprises instructions that, when the program is executed by a computer 10, cause the computer 10 to carry out the steps described above of the method for quality control of a welding joint 16 between a pair of ends of conducting elements of an inductive winding of a stator according to the invention.

The present invention also relates to a computer-readable storage medium comprising instructions which, when the instructions are executed by a computer 10, cause the computer 10 to carry out the steps described above of the method for quality control of a welding joint 16 between a pair of ends of conducting elements of an inductive winding of a stator according to the invention.

In practice it has been found that the present invention fully achieves the set aim and objects. In particular, it has been seen that the method for quality control of a welding joint between a pair of ends of conducting elements of an inductive winding of a stator thus conceived makes it possible to overcome the qualitative limitations of the prior art, in that it makes it possible to obtain better effects than those that can be obtained with conventional solutions and/or similar effects at lower cost and with higher performance levels.

An advantage of the method for quality control of a welding joint between a pair of ends of conducting elements of an inductive winding of a stator according to the present invention consists in that it makes it possible to examine and evaluate welding joints objectively and rapidly.

Another advantage of the method for quality control of a welding joint between a pair of ends of conducting elements of an inductive winding of a stator according to the present invention consists in that it makes it possible to identify and calculate the bare area of the welding joints with high precision.

Another advantage of the method for quality control of a welding joint between a pair of ends of conducting elements of an inductive winding of a stator according to the present invention consists in that it makes it possible to calculate the welded area of the welding joints with high precision.

Another advantage of the method for quality control of a welding joint between a pair of ends of conducting elements of an inductive winding of a stator according to the present invention consists in that it makes it possible to classify each welding joint according to the respective welding quality level.

The invention, thus conceived, is susceptible of numerous modifications and variations, all of which are within the scope of the appended claims. Moreover, all the details may be substituted by other, technically equivalent elements.

In practice the materials employed, provided they are compatible with the specific use, and the contingent dimensions and shapes, may be any according to requirements and to the state of the art.

In conclusion, the scope of protection of the claims shall not be limited by the figures or by the preferred embodiments illustrated in the description by way of examples, but rather the claims shall comprise all the patentable characteristics of novelty that reside in the present invention, including all the characteristics that would be considered as equivalent by the person skilled in the art.

The disclosures in Italian Patent Application No. 102022000002090 from which this application claims priority are incorporated herein by reference.

Where the technical features mentioned in any claim are followed by reference numerals and/or signs, those reference numerals and/or signs have been included for the sole purpose of increasing the intelligibility of the claims and accordingly, such reference numerals and/or signs do not have any limiting effect on the interpretation of each element identified by way of example by such reference numerals and/or signs.

The invention claimed is:

1. A method for quality control of a welding joint between a pair of ends of conducting elements of an inductive winding of a stator, said method being performed by a computer, comprising the steps of:

acquiring a 3D reconstruction of said welding joint;

extracting a white 2D grayscale blob area from said 3D reconstruction of said welding joint, by transversely sectioning said 3D reconstruction with a cutting plane that is arranged at a cutting distance from a peak of said 3D reconstruction, said cutting distance being chosen so that said cutting plane is further downward than a base of said welding joint, and assigning a white color to the area of said 3D reconstruction above said cutting plane in order to determine said 2D grayscale blob area;

calculating a center of mass of said 2D grayscale blob area in order to determine a rotation axis orthogonal to said cutting plane and passing through said center of mass;

extracting a plurality of profiles from said 3D reconstruction of said welding joint, by longitudinally sectioning said 3D reconstruction with a plurality of planes that are orthogonal to said cutting plane, proceeding in rotation about said rotation axis, each orthogonal plane comprising a respective profile of said 3D reconstruction;

searching for and identifying bare zones of said welding joint by analyzing one by one profile portions of said plurality of profiles of said 3D reconstruction, calculating for each profile portion a respective straight interpolation line on points that constitute said profile portion, said profile portion being identified as a bare zone if said respective straight interpolation line has an angular coefficient with an absolute value smaller than or equal to 10°; and calculating a bare area of said welding joint by summing said bare zones identified by the analysis of said plurality of profiles of said 3D reconstruction, a contribution of each bare zone to said bare area being equal to an arc of an annulus comprised between said respective profile portion in which said bare zone has been identified and a following profile portion from the analysis of said plurality of profile portions.

2. The method according to claim 1, further comprising the step of calculating a welded area of said welding joint by subtracting said bare area of said welding joint from said 2D grayscale blob area.

3. The method according to claim 1, further comprising the step of classifying said welding joint according to a respective welding quality level.

4. The method according to claim 1, wherein said step of extracting said white 2D grayscale blob area further comprises the step of orthogonally projecting an upper portion of said 3D reconstruction of said welding joint on said cutting plane.

5. The method according to claim 1, wherein, in said step of extracting said plurality of profile portions, said plurality of orthogonal planes longitudinally sectioning said 3D reconstruction of said welding joint are uniformly distributed in breadth, by rotating with respect to each other through a breadth until a total breadth of no more than 179° is reached.

6. The method according to claim 1, wherein, in said step of searching for and identifying bare zones of said welding joint, a sequence of inspection windows, arranged side by side one after the other, each one of preset width less than the width of said profile portion, slides along each profile portion of said 3D reconstruction, said profile portions being contained in respective inspection windows.

7. The method according to claim 1, wherein said step of searching for and identifying bare zones of said welding joint further comprises the steps of arranging an exclusion plane which transversely sections said 3D reconstruction at an exclusion distance from said peak of said 3D reconstruction, and calculating, for each profile portion, a respective average height of said points that constitute said profile portion, excluding said profile portion if said respective average height is greater than the height of said exclusion plane.

8. The method according to claim 1, wherein said step of searching for and identifying bare zones of said welding joint further comprises the step of counting said bare zones of said welding joint, all of said welding joint being identified as a bare area if the number of said bare zones is greater than a percentage of the number of analyzed profile portions.

9. The method according to claim 1, wherein, in said step of calculating a bare area of said welding joint by summing said bare zones, a contribution of a bare zone arranged at the beginning or at an end of said profile portion to said bare area is weighted on a filling percentage of a respective inspection window.

10. The method according to claim 1, wherein said step of acquiring said 3D reconstruction of said welding joint is performed with said pair of ends of conducting elements oriented vertically and with the base of said ends pointing upward.

11. The method according to claim 1, wherein said welding joint between said pair of ends of conducting elements and said 3D reconstruction of said welding joint) have a same orientation with respect to a common geometric reference system.

12. The method according to claim 1, wherein said step of acquiring said 3D reconstruction of said welding joint is performed with a Fringe Pattern Projection technique.

13. The method according to claim 1, wherein said step of acquiring said 3D reconstruction of said welding joint is performed using a 3D camera or a 3D laser scanning device.

14. A computer comprising means configured to perform the steps of the method according to claim 1.

15. A computer comprising a processor and a memory storing program instructions, which when executed by the processor, cause the computer to carry out the steps of the method according to claim 1.

16. A non-transitory computer-readable storage medium comprising instructions which, when the instructions are executed by a computer, cause the computer to carry out the steps of the method according to claim 1.

* * * * *